United States Patent [19]
Houlihan et al.

[11] 3,962,320

[45] June 8, 1976

[54] BIS-SUBSTITUTED BENZYL ACETIC ACIDS

[75] Inventors: William J. Houlihan, Mountain Lakes; Jeffrey Nadelson, Lake Parsippany, both of N.J.

[73] Assignee: Sandoz, Inc., East Hanover, N.J.

[22] Filed: Jan. 31, 1975

[21] Appl. No.: 545,736

Related U.S. Application Data

[60] Division of Ser. No. 421,673, Dec. 4, 1973, Pat. No. 3,884,961, which is a continuation-in-part of Ser. No. 403,225, Oct. 3, 1973, abandoned, which is a continuation-in-part of Ser. No. 333,892, Feb. 20, 1973, abandoned.

[52] U.S. Cl............................................. 260/515 R
[51] Int. Cl.².................................... C07C 63/33
[58] Field of Search......... 260/515 R, 515 A, 520 R

[56] References Cited
UNITED STATES PATENTS

| | | | |
|---|---|---|---|
| 3,352,901 | 11/1967 | Schultz et al. | 260/476 R |
| 3,352,903 | 11/1967 | Schultz et al. | 260/515 R |
| 3,867,465 | 2/1975 | Houlihan et al. | 260/515 R X |
| 3,870,751 | 3/1975 | Houlihan et al. | 260/515 R |
| 3,907,878 | 9/1975 | Houlihan et al. | 260/515 R |

*Primary Examiner*—James O. Thomas, Jr.
*Assistant Examiner*—G. Breitenstein
*Attorney, Agent, or Firm*—Gerald D. Sharkin; Robert S. Honor

[57] ABSTRACT

Bis-substituted benzyl acetic acids, e.g., bis-(p-pivaloylbenzyl)acetic acid, are prepared by hydrolyzing and decarboxylating a corresponding bis-(p-pivaloylbenzyl)malonic acid diethyl ester and are useful as hypolipidemic agents.

4 Claims, No Drawings

BIS-SUBSTITUTED BENZYL ACETIC ACIDS

This is a division of application Ser. No. 421,673 filed Dec. 4, 1973 now U.S. Pat. No. 3,884,961 which is a continuation-in-part of copending application Ser. No. 403,225, filed Oct. 3, 1973 now abandoned which in turn is a continuation-in-part of copending application Ser. No. 333,892, filed Feb. 20, 1973 now abandoned.

This invention relates to bis-substituted benzyl acetic acids which exhibit hypolipidemic activity. In particular, it relates to substituted benzyl acetic acids, pharmaceutically acceptable salts, their preparation and intermediates thereof.

The compounds of this invention may be represented by the formula:

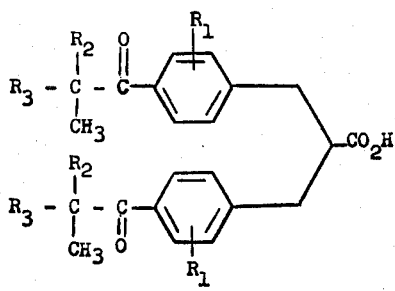

(I)

where
$R_1$ each independently represents hydrogen, halo having an atomic weight of about 19 to 36, and straight chain lower alkoxy, i.e., straight chain alkoxy having 1 to 4 carbon atoms, e.g. and methoxy, ethoxy, isopropoxy or the like and
$R_2$ and $R_3$ each independently represent alkyl having 1 to 2 carbon atoms, i.e. methyl or ethyl.

The compounds of formula (I) are prepared according to the following reaction scheme:

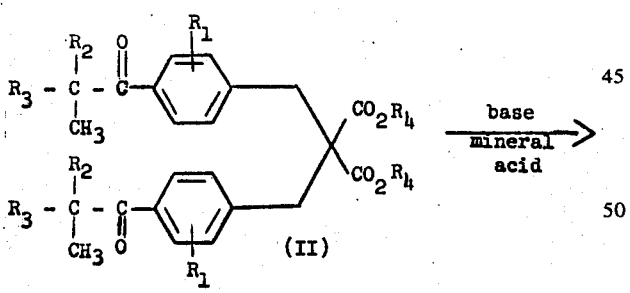

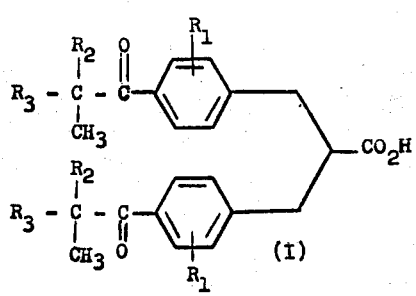

where $R_4$ each independently represents lower alkyl having 1 to 4 carbon atoms, e.g. methyl, ethyl, isopropyl and the like, and
$R_1$, $R_2$ and $R_3$ are as defined above.

The compounds of formula (I) are prepared by hydrolyzing and decarboxylating a compound of the formula (II). The compounds of formula (II) are hydrolyzed employing conventional techniques with an alkali metal base such as sodium or potassium hydroxide, the latter being especially preferred, followed by acidification and spontaneous decarboxylation using a mineral acid in the presence of an aqueous solvent. Suitable acids which can be employed include hydrochloric acid, sulfuric acid and hydrobromic acid, preferably hydrochloric acid. The aqueous solvent can be water or a mixture of water and a water soluble organic solvent e.g., lower alkanols having 1 to 4 carbon atoms e.g. methanol, ethanol and the like. The temperature of the reaction is not critical, but it is preferred that the reaction be carried out at the reflux temperature of the solvent. The reaction is run from about 12 to 36 hours, preferably about 15 to 20 hours. The product is recovered by conventional techniques e.g. crystallization.

The compounds of formula (II) are prepared according to the following reaction scheme:

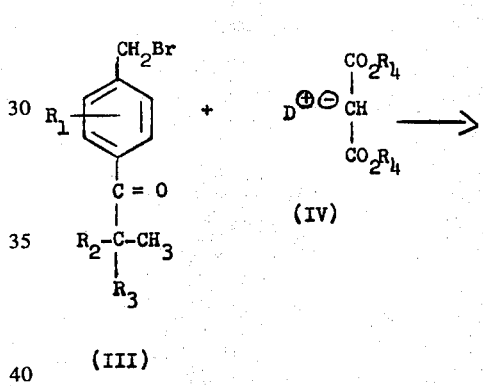

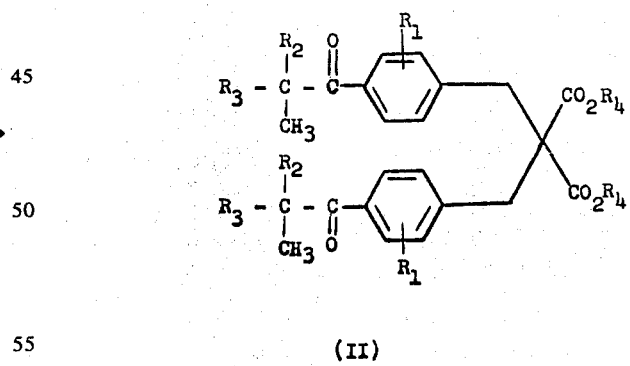

where
D is an alkali metal such as sodium or potassium and $R_1, R_2, R_3$ and $R_4$ are as defined above.

The compounds of formula (II) are prepared by treating a compound of the formula (III) with a compound of the formula (IV) in the presence of a strong base such as sodium hydride, potassium hydride, sodium ethoxide or potassium ethoxide, the latter being especially preferred for increase yields. The reaction is carried out in the presence of an inert organic solvent such as lower alkanols, methanol, ethanol and the like, dimethylformamide or dimethylacetamied, the latter being especially preferred. The temperature of the reaction is not critical, but it is preferred that the reaction be run from about 20° to 30°C, preferably about 25°C. The reaction is run from about 12 to 24 hours, preferably about 16 to 20 hours. The product is recovered using conventional techniques eg, crystallization.

The compounds of formula (III) are prepared according to the following reaction scheme:

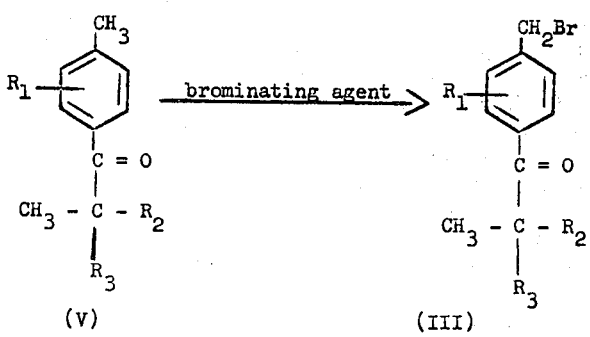

where $R_1$, $R_2$ and $R_3$ are as defined above.

The compounds of formula (III) are prepared by treating a compound of formula (V) with a brominating agent in the presence of an inert organic solvent and free radical initiator. The brominating agent which can be used is bromine, N-bromosuccinimide, N-bromo phthalamide, N-bromo-acetamide and the like. The particular agent used is not critical, but N-bromosuccinamide is preferred. In the preferred process, the free radical initiator used is an organic peroxide, especially benzoyl peroxide. The reaction can also be carried out under ultraviolet light. Although the particular solvent used is not critical, the preferred solvents are the halogenated hydrocarbons such as methylene dichloride, chloroform carbon tetrachloride and the like, although the aromatic hydrocarbons such as benzene can also be employed. The temperature of the reaction is not critical, but reflux temperature of the solvent is preferred. The reaction is run for about 12 to 48 hours; preferably about 18 to 25 hours. The product is recovered by conventional techniques, e.g., crystallization.

Many of the compounds of formula (IV) and (V) are known and may be prepared by methods described in the literature. The compounds of formula (IV) and (V) not specifically disclosed may be prepared by analogous methods from known starting materials.

It will be understood that certain of the compounds of formulae (I) and (II) in which the benzyl groups are not identical may exist in the form of optically active isomers. The separation and recovery of the respective isomers may be readily accomplished employing conventional techniques and such isomers are included within the scope of the invention.

The compounds of formulae (I) and (II) are useful because they possess pharmacological activity in animals as hypolipidemic agents, particularly as hyperlipoproteinemic agents as indicated by the fall in cholesterol and triglyceride levels in male albino Wistar rats weighing 110-130 g initially. The rats are maintained on drug-free laboratory chow diet for seven days and then divided into groups of 8 to 10 animals. Each group with the exception of the control is then given orally 30 milligrams per kilogram of body weight per diem of the compound for six days. At the end of this period, the animals are anesthetized with sodium hexobarbital and bled from the carotid arteries. Serum or plasma samples are collected, and 1.0 ml samples of the serum are added to 9.0 ml redistilled isopropanol. Two autoanalyzer cupsful of a mixture of zeolite-copper hydroxide and Lloydds reagent (Kessler, G., and Lederer, H., 1965, *Technicon Symposium*, Mediad Inc., New York, (345–347) are added, and the mixture is shaken for one hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) and (II) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups and elixirs and parenterally as solutions, suspensions, dispersions, emulsions and the like, e.g. a sterile injectable aqueous solution. The dosage will vary depending upon the mode of administration utilized and the particular compound employed.

The compounds of formula (I) may be similarly administered in the form of their non-toxic pharmaceutically acceptable salts. Such salts possess the same order of activity as the free acid, and are readily prepared by reacting the acid with an appropriate hydroxide or oxide and, accordingly, are included within the scope of this invention. Representative of such salts are the alkali metal salts, e.g. sodium, potassium and the like, and the alkaline earth metal salts such as magnesium, calcium and the like.

The hypolipidemic effective dosage of compounds (I) and (II) employed in the alleviation of lipidemia may vary depending on the particular compound employed and the severity of the condition being treated. However, in general, satisfactory results are obtained when the compounds of formulae (I) and (II) are administered at a daily dosage of from about 2.0 milligrams to about 250 milligrams per kilogram of animal body weight, preferably 10.0 milligrams to about 250 milligrams per kilogram given in divided doses two to four times a day, or in sustained release form. For most large mammals, the total daily dosage is from about 150 milligrams to about 3000 milligrams, preferably 700 milligrams to 3000 milligrams. Dosage forms suitable for internal use comprise from about 37.5 to about 1500 milligrams of the active compound in intimate admixture with a solid or liquid pharmaceutically acceptable carrier or diluent.

A representative formulation suitable for oral administration 2 to 4 times a day for the treatment of lipidemia is a capsule prepared by standard encapsulating techniques which contains the following:

| Ingredients | Weight (mg) |
| --- | --- |
| bis-(p-pivaloylbenzyl)acetic acid | 150 |
| inert solid diluent (starch, lactose, kaolin.) | 300 |

EXAMPLE 1

α-bromo-p-pivaloyl toluene

To a suspension of 28.5 g (1.17 g. atoms) magnesium turnings in 150 ml tetrahydrofuran under a nitrogen atmosphere there is added 10 ml of 4-bromotoluene (1.17 mole) in 650 ml dry tetrahydrofuran, the reaction is started and the remainder of the bromotoluene solution is added dropwise at a rate that maintains a moderate reflux. After the addition is complete, the mixture is refluxed for an additional 1½ hours. The resulting Grignard solution is added dropwise to a cold solution of 128.0 g pivaloyl chloride (1.06 mole) in 500 ml dry tetrahydrofuran at a rate that maintains the temperature at 0° to −5°C. The solution is stirred for an additional 1½ hours at 0° and then at room temperature for 18 hours. The mixture is then cooled to 0° and hydrolyzed by the addition of 100 ml 2N hydrochloric acid. The layers are separated and 200 ml of ether is added to the organic phases which is then washed respectively with 100 ml 2N hydrochloric acid, 100 ml. 10% sodium bicarbonate solution and 100 ml. saturated sodium chloride. The resulting layer is dried over anhydrous sodium sulfate, filtered, and the solvent is removed in vacuo to give p-pivaloyl toluene (b.p 80°–84°C/0.7 mm, $n_D^{21}$ 1.5108). A mixture of 156.3 g. (0.886 mole) of the resulting p-pivaloyl toluene is then added to 157.8 g. (0.886) mole) N-bromosuccinimide, 4.0 g (0.016 mole) benzoyl peroxide and 150 ml. carbon tetrachloride and heated at reflux for 18 hours. The mixture is cooled and filtered and the resulting precipitate is washed with carbon tetrachloride. The solvents are removed in vacuo and the resulting oil is distilled in vacuo to give α-bromo-p-pivaloyl toluene (b.p. 124°–132°/ 0.7 mm, $n_D^{22}$ 1.5546- V.P.C.96% monobromo 4%-dibromo).

Following the above procedure and using in place of 4-bromotoluene equivalent amounts of:
a. 4-bromo-2-chlorotoluene or
b. 4-bromo-2-methoxytoluene,
there is obtained
a. α-bromo-2-chloro-4-pivaloyl toluene or
b. α-bromo-2-methoxy-4-pivaloyl toluene, respectively.

EXAMPLE 2 bis-(p-pivaloyl benzyl)malonic acid diethyl ester

To a cold suspension of 4.66 g (0.194) mole of sodium hydride in 200 ml dimethylacetamide there is added dropwise 28.2 g (0.176 mole) diethyl malonate in 80 ml of dimethylacetamide maintaining the temperature between 0° and 5°C. Stirring is initiated for two hours at room-temperature and there is then added 40.8 g(0.16 mole) of α-bromo-p-pivaloyl toluene in 200 ml of dimethylacetamide maintaining the reaction temperature between 20° and 30°C. Stirring is continued overnight at room temperature. Water is then added and the excess dimethylacetamide is removed in vacuo, and the resulting residue is partitioned between petroleum ether and water. The layers are washed with water, and salt water, dried and evaporated in vacuo. The residue is then distilled in vacuo and crystallized from petroleum ether at −50°C to give bis-(p-pivaloylbenzyl)malonic acid diethyl ester, m.p. 65° to 67°C.

Following the above procedure and using in place of α-bromo-p-pivaloyl toluene an equivalent amount of
a. α-bromo-2-chloro-4-pivaloyl toluene, or
b. α-bromo-2-methoxy-4-pivaloyl toluene,
there is obtained
a. bis-(2-chloro-p-pivaloylbenzyl)malonic acid diethyl ester, or
b. bis-(2-methoxy-p-pivaloylbenzyl)malonic acid diethyl ester, respectively.

The bis-(p-pivaloylbenzyl)malonic acid diethyl ester of this example is an effective hypolipidemic agent when orally administered to an animal suffering from lipidemia at a dosage of 150 mg. four times per day.

EXAMPLE 3 bis-(p-pivaloylbenzyl)acetic acid

To a solution of 10g (0.03 mole) of bis-(p-pivaloylbenzyl) malonic acid diethyl ester in 45 ml of ethanol and 45 ml of water, there is added 8.4 g (0.15 mole) potassium hydroxide which is refluxed for 5 hours. The solvents are removed in vacuo and the residue partitioned between ether and water. The aqueous layer is made acidic at 0°C with concentrated hydrochloric acid, extracted with ether, dried and evaporated. The resulting oil is treated with 200 ml of concentrated hydrochloric acid and the mixture is refluxed for 20 hours. The cooled mixture is extracted with ether, the ether extracted with 2N sodium hydroxide and the basic solution is made acidic at 0°C with concentrated hydrochloric acid, extracted with ether, and the ether is then dried and evaporated. The resulting residue is crystallized from ether/petroleum ether to give bis-(p-pivaloylbenzyl) acetic acid, m.p. 107°–109°C.

Following the above procedure and using in place of bis-(p-pivaloylbenzyl) malonic acid diethyl ester an equivalent amount of
a. bis-(2-chloro-p-pivaloylbenzyl)malonic acid diethyl ester, or
b. bis-(2-methoxy-p-pivaloylbenzyl)malonic acid diethyl ester there is obtained
a. bis-(2-chloro-p-pivaloylbenzyl)acetic acid, or
b. bis-(2-methoxy-p-pivaloylbenzyl)acetic acid, respectively.

The bis-(p-pivaloylbenzyl)acetic acid of this example is an effective hypolipidemic agent when orally administered to an animal suffering from lipidemia at a dosage of 150 mg four times per day.

What is claimed is:
1. A compound of the formula:

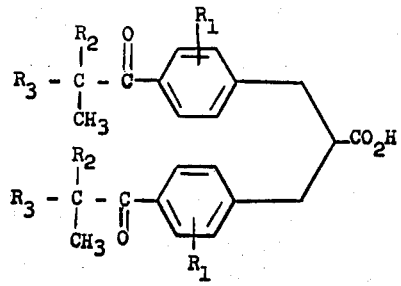

where
$R_1$ each independently represents hydrogen, fluorine, chlorine or straight chain lower alkoxy, and
$R_2$ and $R_3$ each independently represent lower alkyl having 1 to 2 carbon atoms or a pharmaceutically acceptable salt thereof.

2. A compound of the formula

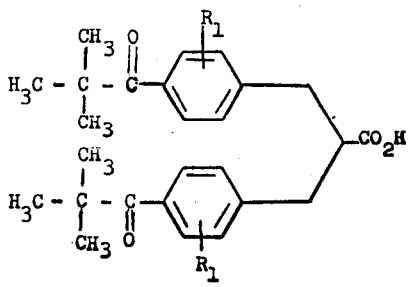
where $R_1$ is as defined in claim 1, or a pharmaceutically acceptable salt thereof.
3. A compound of the formula
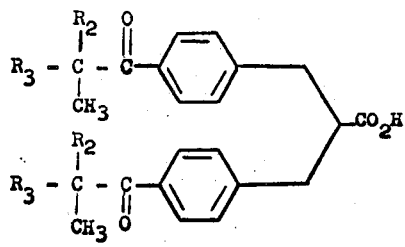
where $R_2$ and $R_3$ are as defined in claim 1, or a pharmaceutically acceptable salt thereof.
4. The compound of claim 1 which is bis-(p-pivaloylbenzyl)acetic acid.
* * * * *